(12) United States Patent
Lehn et al.

(10) Patent No.: US 7,522,277 B2
(45) Date of Patent: Apr. 21, 2009

(54) LATERAL SURFACE SENSOR AND IMAGING OPTICAL SYSTEM THEREFOR

(75) Inventors: Norbert Lehn, Taunusstein (DE); Martin Schumacher, Schlangenbad (DE)

(73) Assignee: Vitronic Dr. Ing. Stein Bildverarbeitungssysteme GmbH, Wiesbaden (DE)

( * ) Notice: Subject to any disclaimer, the term of this patent is extended or adjusted under 35 U.S.C. 154(b) by 323 days.

(21) Appl. No.: 10/548,922

(22) PCT Filed: Mar. 12, 2004

(86) PCT No.: PCT/EP2004/050305

§ 371 (c)(1),
(2), (4) Date: Sep. 9, 2005

(87) PCT Pub. No.: WO2004/083777

PCT Pub. Date: Sep. 30, 2004

(65) Prior Publication Data

US 2006/0176474 A1    Aug. 10, 2006

(30) Foreign Application Priority Data

Mar. 18, 2003    (DE) ................................ 103 12 051

(51) Int. Cl.
*G01N 21/00* (2006.01)
*G01N 9/04* (2006.01)

(52) U.S. Cl. .............. 356/239.1; 356/239.2; 356/239.4; 250/223 B

(58) Field of Classification Search ... 356/239.1–239.8, 356/240.1, 237.1–237.2; 250/223 B, 227.11; 209/526

See application file for complete search history.

(56) References Cited

U.S. PATENT DOCUMENTS

| | | | | |
|---|---|---|---|---|
| 4,025,201 A * | 5/1977 | Deane | ...................... 356/239.4 |
| 5,030,823 A * | 7/1991 | Obdeijn | ................... 250/223 B |
| 5,072,107 A * | 12/1991 | Apter | ..................... 250/223 B |
| 5,661,294 A | 8/1997 | Buchmann | |
| 5,669,152 A * | 9/1997 | McMurtry | .................... 33/559 |
| 5,905,595 A * | 5/1999 | Minami | ...................... 359/618 |
| 5,912,776 A * | 6/1999 | Yaginuma | ................... 359/850 |
| 6,072,575 A | 6/2000 | Loell | |
| 6,654,116 B1 * | 11/2003 | Kwirandt | ................. 356/240.1 |
| 6,825,925 B2 * | 11/2004 | Yagita | ..................... 356/240.1 |

FOREIGN PATENT DOCUMENTS

| EP | 0 209 077 A | 1/1987 |
|---|---|---|
| JP | 55 027918 A | 2/1980 |

* cited by examiner

*Primary Examiner*—Sang Nguyen
(74) *Attorney, Agent, or Firm*—Paul & Paul

(57) ABSTRACT

The present invention relates to an imaging optical system for imaging the peripherally extending lateral surfaces (9) of an object (10) on to an imaging plane, comprising a reflecting element (6) and a first angle-reducing element (3, 17) which is arranged downstream of the reflecting element in the beam direction and which reduces the angle between a light beam emanating from the object (10) and the optical axis (12). In order to provide an imaging optical system for imaging the peripherally extending lateral surfaces of objects, which is both simple and inexpensive to produce and also has a large acceptance angle for the incident radiation and which is tolerant in relation to inaccurate positioning of the object, it is proposed in accordance with the invention that arranged upstream of the reflecting element (6) in the beam direction is a second angle-reducing element (13) which reduces the angle between a light beam (1, 1) emanating from the object (10) and the optical axis (12).

49 Claims, 4 Drawing Sheets

LATERAL SURFACE SENSOR AND IMAGING OPTICAL SYSTEM THEREFOR

The present invention concerns an imaging optical system for imaging the peripherally extending lateral surfaces of an object on to an imaging plane comprising a reflecting element and a first angle-reducing element which is arranged downstream of the reflecting element in the beam direction and which reduces the angle between a light beam emanating from the object and the optical axis.

Various production processes require inspection of the peripherally extending lateral surfaces of rotationally symmetrical objects. For example the necks of drinks bottles must be examined for contamination after the bottles have been filled. In that respect it is important for the object to be detected from all sides so that a single, laterally arranged camera is not sufficient.

If markings, for example date imprints, are to be detected on the lateral surfaces of objects involving rotational symmetry, it is only possible to ensure at a high level of expenditure, during a production process, that the object is so oriented for example on a conveyor belt that the imprint is pointing in the direction of the one camera.

If in contrast the attempt is made to view the entire periphery of the object for example by providing four cameras which each detect a peripheral angle of 90°, evaluation of the images is made difficult in particular when for example the text printed thereon is positioned in such a way that it is detected in parts thereof by different cameras. Evaluation of the items of information obtained by the four cameras is very complicated and expensive in particular in the overlap regions as it is precisely in those regions that the individual images involve considerable distortion.

Therefore, the state of the art discloses inspection systems which make it possible to detect both the inner and also the outer peripherally extending lateral surfaces of an object with a camera arranged above the object by means of a symmetrical lens or mirror optical system.

DE 31 09 270 shows for example an inspection system for checking bottle necks for contamination and impurities and damage with a single television camera. In that arrangement the optical system which forms the image of the outside wall of the bottle alternatively comprises a convergent lens of large diameter or an internally mirrored tube which can be at least partially pushed over the bottle neck.

DE 42 09 417 discloses an optical checking device for female screwthreads, wherein the image of the female screwthread is produced by means of a conical mirror on the sensor surface of a camera, which is arranged perpendicularly to the axis of symmetry of the screwthread.

DE 30 35 082 describes an inspection system which is also intended to be capable of detecting those surface regions which are in the shadow of the direction of view of a television camera. For that purpose the light beams which are reflected at the surface of the object are firstly reflected symmetrically with respect to the axis of rotation of the object twice at different angles and at the second reflection are projected into a plane which is perpendicular to the axis of rotation. Reflection is effected by means of a mirror system which is rotationally symmetrical in itself and with respect to the axis of rotation of the object and which comprises a conical mirror and a frustoconical hollow mirror. In that arrangement the two mirrors are disposed concentrically around the axis of rotation of the object. The mirroring surface of the conical mirror is towards the television camera and is inclined relative to the axis of rotation of the object more greatly than the mirroring surface of the frustoconical hollow mirror which is towards the rotationally symmetrical object.

DE 197 26 967 which builds on DE 30 35 082 describes an inspection system whose deflection optical arrangement is modified in such a way that that the outwardly disposed reflection surface extends in a substantially tubular configuration around the optical axis and surrounds the inwardly disposed reflection surface concentrically, leaving a light passage, wherein the inwardly disposed reflection surface is of a cross-section, corresponding to the outwardly disposed reflection surface, perpendicularly to the optical axis, and extends at an acute angle which opens towards the object, relative to the optical axis, so that light beams extending parallel to the optical axis are deflected from the inwardly disposed reflection surface on to the outwardly disposed reflection surface and are there reflected with an acute viewing angle on to the peripherally extending lateral surface.

The above-discussed state of the art has the common difficulty that the two concentric mirror elements have to be fixed relative to each other, which is complicated and expensive. In addition the acceptance angle of the mirror optical arrangement for the light beams emanating from the object is limited by the distance between the outer and inner mirrors. The limitation on the acceptance angle means that, in the arrangement described in DE 197 26 967, the beams emanating from the object impinge on the outwardly disposed reflection surface at a shallow angle. Minor deviations in the position of the object from the symmetrical position in which the axis of symmetry of the object and the deflection optical arrangement coincide therefore already mean that the images of the lateral surfaces are no longer produced on the camera.

DE 197 26 967 also describes an embodiment of the apparatus, in which the light beam deflection device is formed by a cylindrical or polygonal prism body. The outwardly disposed reflection surface is formed by the totally reflecting external boundary surface of the prism body and the inwardly disposed reflection surface is formed by the totally reflecting boundary surface of a conical or frustoconical, or polygonal pyramid or truncated pyramid-shaped recess, which is open towards the object, in the prism body. The recess is of such a configuration that the beams emanating from the object impinge on the lateral surfaces of the recess at a right angle. In this embodiment in the state of the art the acceptance angle of the deflection optical arrangement for the incident light beams is restricted by the critical angle of incidence of total reflection. The angle is not to fall below that angle either upon total reflection at the outer boundary surface of the prism body or upon total reflection at the recess. Light beams which only very shallowly impinge on the boundary surfaces of the prism body are totally reflected. With this beam path however a slight deviation in respect of the object relative to an optical axis of the imaging optical system already has the effect that the entire image of the lateral surfaces of the object is no longer produced on the camera.

In comparison with that state of the art the object of the present invention is to provide an imaging optical system for imaging the peripherally extending lateral surfaces of objects, which is both simple and inexpensive to produce and which also has a large acceptance angle for the incident radiation and which is tolerant in relation to inaccurate positioning of the object.

The object of the invention is attained in that the imaging optical system for imaging the peripherally extending lateral surfaces of an object on to an imaging plane comprises a reflecting element and a first angle-reducing element which is arranged downstream of the reflecting element in the beam direction and which reduces the angle between a light beam emanating from the object and the optical axis, and that arranged upstream of the reflecting element in the beam direction is a second angle-reducing element which reduces the angle between a light beam emanating from the object and the optical axis. That configuration of the imaging optical system is desirable as the light beams incident in the imaging optical system are firstly deflected at the second angle-reducing element and thus their angle relative to the optical axis is reduced. Therefore even beams which pass into the optical system at a shallow angle can be imaged.

In a preferred embodiment the reflection surface of the reflecting element is of a rotationally symmetrical, preferably circular cross-section in a plane extending perpendicularly to the optical axis. That is advantageous as such a symmetry is matched to the symmetry of peripherally extending lateral surfaces. That applies both in respect of bodies of a circular or oval cross-section and also bodies with non-oriented polygonal base surfaces. It is desirable in that respect if at least one of the angle-reducing elements is of a rotationally symmetrical, preferably circular cross-section in a plane extending perpendicularly to the optical axis. It is particularly advantageous however if the two angle-reducing elements are of a rotationally symmetrical cross-section in a plane extending perpendicularly to the optical axis.

In a further embodiment of the invention the second angle-reducing element is formed by a boundary surface of a transparent body so that angle reduction is effected by refraction of the light beam when the light beam passes into the transparent body. That allows the second angle-reducing element to be of a simple configuration as a flat surface already provides for refraction in a direction towards the optical axis.

It is advantageous if the refractive boundary surface includes with the optical axis an angle of between 60° and 120°, preferably between 80° and 100°, particularly preferably between 85° and 95° and best an angle of about 90°. That choice of the angle between the boundary surface of the transparent body and the optical axis in the specified range permits an optimum acceptance angle for the imaging optical system.

In a preferred embodiment of the invention the reflection surface of the reflecting element is formed by a boundary surface of a transparent body. Such transparent bodies can be produced inexpensively, at a high level of surface quality. Reflection at the boundary surface can take place by virtue of internal total reflection so that no mirroring of the boundary surface is required. If in contrast the boundary surface is additionally mirrored, the acceptance angle of the imaging optical system is increased as it is not necessary to observe any limiting angles for total reflection.

It is desirable if the boundary surfaces which form the reflecting element and the second angle-reducing element are boundary surfaces of the same transparent body. It is then only necessary to produce one element which performs both tasks. In that respect a particularly preferred embodiment is one in which the transparent body is a transparent cylinder. Such an element can be easily produced even in large numbers and, by virtue of its high degree of symmetry, is excellently well suited for imaging rotationally symmetrical objects and in addition can also be used with advantage for imaging objects of any other symmetry.

A preferred embodiment of the invention is one in which the transparent body comprises glass. By virtue of the choice of a glass with a suitable refractive index, it is possible to adapt the angle reduction effect. It can also be desirable for the transparent body to be made from a transparent plastic material so that the imaging optical system is reduced in weight.

An advantageous embodiment of the invention is one in which the first angle-reducing element has a reflecting or refracting surface which is so oriented that angle reduction is effected by reflection or refraction of the light beam.

A particularly preferred embodiment of the invention is one in which the reflecting or refracting surface of the first angle-reducing element is the peripheral surface of a cone or a truncated cone. Such a shape is adapted by virtue of its symmetry to the rotationally symmetrical objects and permits uniform deflection of all impinging beams.

It is desirable if the first angle-reducing element comprises metal, preferably aluminum, and its reflecting surfaces are preferably polished. Such an element can be easily produced and already has an adequate level of surface quality for aberration-free imaging. In order to achieve particularly high levels of surface quality, it can be desirable for the first angle-reducing element to be made from plastic material or glass with mirrored reflecting surfaces. If the element is made from plastic material that additionally affords an advantageous reduction in weight.

A particularly preferred embodiment of the invention is one in which the surface of the first angle-reducing element is the peripheral surface of a truncated cone and the cover surface of the truncated cone has a central bore. That configuration, besides imaging the lateral surfaces of the object by means of the imaging optical system, also permits the cover surface of the object to be imaged with a direct beam path through the hole in the truncated cone on to the camera. It is desirable with this embodiment if the glass body also has a central bore in alignment with the central bore in the mirror body. That permits a direct beam path from the cover surface of the object to the camera without losses at the reflecting surfaces of the glass body.

It may be desirable if the first angle-reducing element is formed by the boundary surface of a transparent body so that angle reduction is effected by refraction of the light beam when the light beam issues from the transparent body. Such a configuration is particularly advantageous when the boundary surfaces of the transparent bodies which form the reflecting element and the first and second angle-reducing elements are boundary surfaces of the same transparent body. The imaging optical system then comprises only one element which is simple to mount and which after production does not have to be further adjusted.

A preferred embodiment of the invention is one in which the ratio of the diameter of the first angle-reducing element to the diameter of the second angle-reducing element is less than 1 and preferably between ½ and ¼. Such a configuration permits optimum imaging in particular of the lateral surfaces of cover caps of a typical maximum diameter of about 30 mm.

It is further advantageous if the height of the transparent body is between 10 mm and 100 mm, preferably between 20 mm and 90 mm, particularly preferably between 30 mm and 80 mm and best about 45 mm.

A particularly desirable embodiment of the invention is one in which the first angle-reducing element is of a height of between 5 mm and 35 mm, preferably between 10 mm and 30 mm, particularly preferably between 15 mm and 25 mm and at best a height of about 20 mm.

In a preferred embodiment of the invention the imaging optical system is integrated into a peripheral surface sensor which detects the peripherally extending lateral surfaces of an object with an image sensor, preferably a camera. Such an arrangement can be integrated into continuous production processes in order to detect and evaluate the lateral surfaces of rotationally symmetrical objects.

In a particularly preferred embodiment the peripheral surface sensor has a light barrier arrangement which detects the objects under the imaging optical system. That makes it possible to control the moment in time of recording in such a way that the objects which are disposed for example on a conveyor belt are disposed under the imaging optical system at the moment of recording so that the axes of symmetry of the imaging optical system and the object coincide.

It can also be desirable for the peripheral surface sensor to be equipped with a preferably annular flash-like lighting arrangement which is preferably intended to produce light flashes. That ensures uniform brightness of the image recorded by the camera. As an alternative to a lighting arrangement with light flashes, it can be advantageous if the camera can be operated with a short exposure time.

Further advantages, features and possible uses of the present invention will be apparent from the description hereinafter of preferred embodiments and the accompanying Figures in which.

Figure 1:
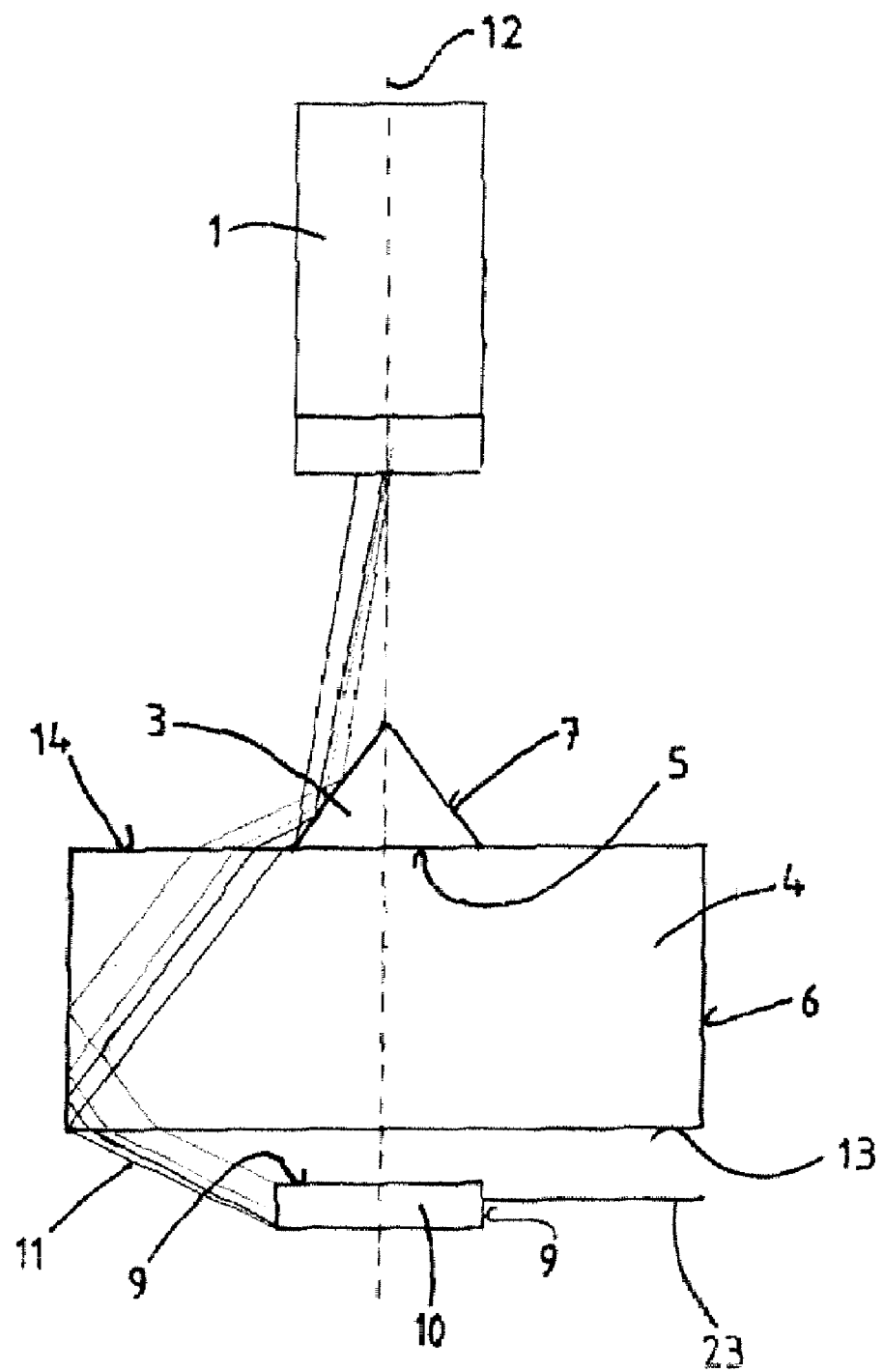
FIG. 1 is a diagrammatic view of a first embodiment of the invention.

FIG. 1 shows an embodiment of the imaging optical system which has a conical mirror body 3 and a transparent cylindrical glass body 4. The components are so arranged that their optical axes 12 coincide with the axis of symmetry of the object 10 which is also cylindrical. The cylindrical glass body 4 and the conical mirror body 3 are arranged above the object 10. The light beams 11 emanating from the lateral surfaces 9 of the object 10 pass into the glass body 4 at a large angle of incidence which is measured towards the perpendicular of incidence. The beams 11 are refracted at the lower cover surface 13 of the glass body. They thereupon pass very shallowly on to the peripheral surface 6 of the glass body 4. As they exceed the critical angle in relation to the normal to the peripheral surface, they are totally reflected at the boundary surface between optically denser and optically thinner medium. In that situation the beams 11 experience a deflection towards the axis of symmetry 12 of the arrangement. The beams 11 issue from the glass body 4 at the upper cover surface 14 thereof. In that case they experience further refraction in a direction towards the axis of symmetry 12. The conical mirror body 3 is disposed directly on the upper cover surface 14 of the glass body 4 and preferably joined thereto by adhesive. Now, the light beams 11 are reflected at the conical peripheral surface 7 of the mirror body 3 in such a way that they impinge on the camera 1 at an acute angle. For objects of a diameter of about 33 mm the diameter of the glass body 4 is preferably 100 mm and the diameter of the base surface 5 of the conical mirror body 3 is preferably 30 mm. In order in that case to be able to completely image the peripheral surface 9 of the object 10, that surface being about 7 mm high, with complete use being made of the resolution involved, the glass body 4 is preferably of a height of 45 mm and the conical mirror body 3 is preferably 20 mm in height. The acceptance angle of the imaging optical system for the beams emanating from the lateral surfaces 9 of the object 10 is about 63.2° with this arrangement. A light barrier arrangement 23 which detects the object under the imaging system is depicted schematically.

Figure 2:
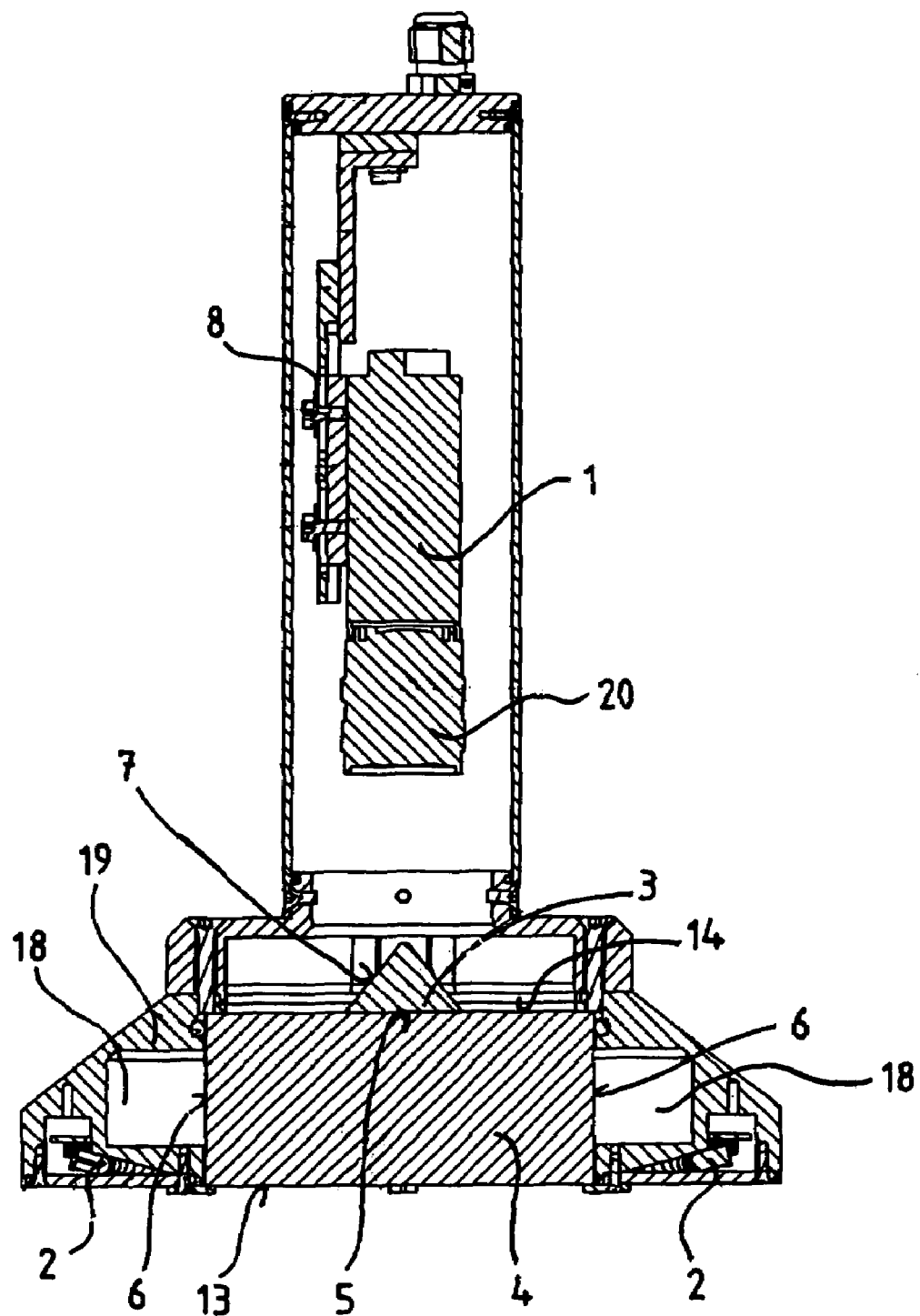
FIG. 2 is a lateral view in section of a first embodiment.

FIG. 2 shows a lateral view in section through a peripheral surface sensor equipped with the imaging optical system diagrammatically shown in FIG. 1. In the illustrated embodiment a lighting means 2 comprising periodically arranged light emitting diodes is mounted in an annular configuration around the glass body 4. The diodes are so oriented that they primarily illuminate the peripheral surface 9 of the object 10. If the objects move quickly under the imaging optical system, it is desirable for the diodes to be operated in such a way that they produce light flashes. FIG. 2 clearly shows a recess 18 in the housing 19, which annularly surrounds the glass body 4. The recess 18 prevents the regions of the peripheral surface 6 of the glass body 4 from coming into contact with the housing 19. In that way the refractive index transition which is necessary for internal total reflection, from the optically denser to the optically thinner medium, is still guaranteed. In addition the recess 18 permits a reduction in the weight of the peripheral surface sensor. The camera 1 with the objective lens 20 fitted thereon can be clearly seen in FIG. 2 above the conical mirror body 3. The camera 1 is fixed adjustably in respect of height on a holder 8. By means of heightwise adjustment of the camera, the apparatus can be adapted to differing diameters of the object 10, while retaining the size of the imaging. The smaller the diameter of the object 10, the correspondingly greater must be the distance adopted between the camera 1 and the conical mirror body 3.

In the illustrated embodiment the transparent body 4 comprises glass. It can however also be made from a transparent plastic material, preferably TPX or PE in order to reduce the mass of the peripheral surface sensor. The mirror body 3 is preferably turned from aluminum and the peripheral surface 7 of the cone is subsequently polished.

The entire apparatus shown in FIG. 2 is mounted in such a way that it can be moved in a plane perpendicular to the axis of symmetry 12 of the object 10, preferably by means of a motor, in order to be able to adjust the deflection axis centrally above the object 10. In that case, an embodiment of the optical means used, of low weight, is desirable.

Figure 3:
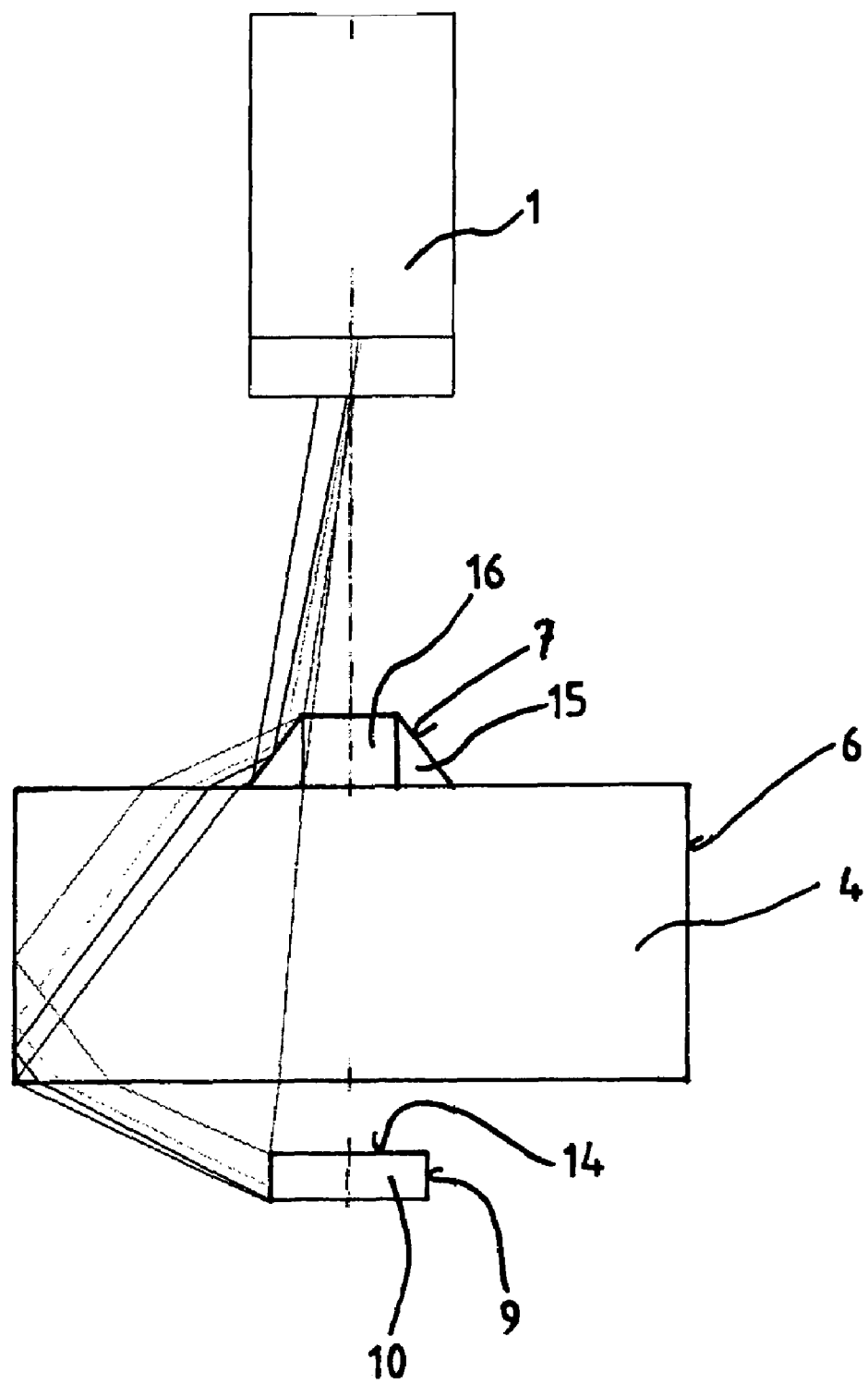
FIG. 3 is a diagrammatic view of a second embodiment.

FIG. 3 shows a second embodiment of the invention in which the conical mirror body 3 has been replaced by a frustoconical mirror body 15. The truncated cone is provided centrally with a central bore 16. A beam path opens through the bore 16 near the optical axis 12, that beam path also making it possible for a beam path emanating from the cover surface 14 of the object 10 to be passed directly on to the camera 1 in addition to the deflected beam path which emanates from the lateral surfaces 9 of the object 10. In addition (not shown in FIG. 3) the glass body 4 can also be provided with a bore in concentric relationship with the bore 16 in the frustoconical mirror body 15. That reduces the reflection losses which otherwise occur at the cover surfaces of the glass cylinder 4.

Figure 4:
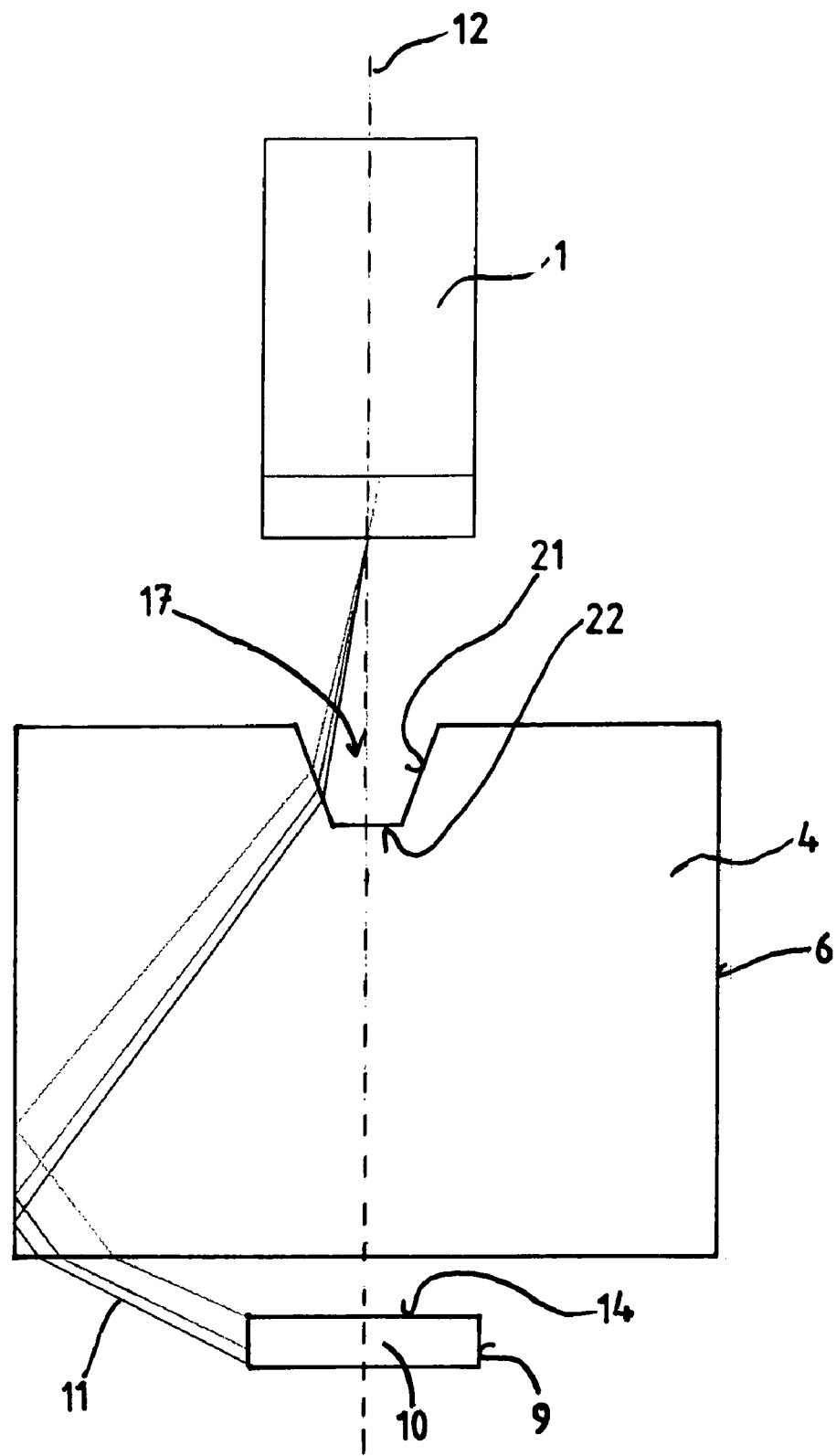
FIG. 4 is a diagrammatic view of a third embodiment.

FIG. 4 shows a third embodiment of the invention in which the imaging optical system comprises only a cylindrical glass body 4 which, starting from the upper cover surface 14, has a central recess 17 in the form of a truncated cone. Beams which emanate from the lateral surfaces 9 of the object 10, on passing into the glass body 4, are refracted by the lower cover surface 13 in such a way that they are totally reflected upon impinging on the peripheral surface 6 of the glass body 4 and are deflected in the direction of the axis of symmetry 12. The beams pass out of the glass body 4 through the peripheral surface 21 of the frustoconical recess 17 in the cover surface 14 of the glass body 4. In that case the beams 11 are so refracted that they impinge on the camera 1 at an acute angle. At the same time, a beam path, starting from the cover surface 14 of the object 10, is possible through the cover surface 22 of the frustoconical recess 11, which produces the image of the cover surface 14 of the object 10 directly on the camera 1.

LIST OF REFERENCES

1 camera
2 annular lighting means
3 conical mirror body
4 cylindrical glass body
5 base surface of the mirror body
6 peripheral surface of the glass body
7 peripheral surface of the mirror body
8 holding means
9 peripherally extending lateral surfaces
10 object
11 light beams
12 optical axis
13 lower cover surface of the glass body
14 upper cover surface of the glass body
15 frustoconical mirror body
16 central bore
17 central recess
18 recess
19 housing
20 objective lens
21 peripheral surface of the recess
22 cover surface of the recess

The invention claimed is:

1. An imaging optical system for directing a light beam along a path emanating from peripherally extending lateral surfaces of an object to an imaging plane comprising:
   a reflecting element;
   a first angle-reducing element arranged downstream along the path in the direction of the light beam after said reflecting element, said first angle-reducing element being capable of reducing the angle between the light beam and an optical axis; and
   a second angle-reducing element arranged upstream from said reflecting element along the path against the direction of the light beam, said second angle-reducing element being capable of reducing the angle between the light beam and the optical axis;
   wherein said first angle-reducing element has a surface being one of a reflecting surface and a refracting surface, said surface being a peripheral surface of a cone and is so oriented that angle reduction is effected by one of reflection and refraction of the light beam, and wherein said reflecting element has a reflection surface formed by a boundary surface of a transparent cylinder.

2. An imaging optical system according to claim 1 characterised in that the reflection surface of the reflecting element is of a rotationally symmetrical cross-section in a plane extending perpendicularly to the optical axis.

3. An imaging optical system according to one of claims 1 and 2 characterised in that at least one of said first and second angle-reducing element is of a rotationally symmetrical cross-section in a plane extending perpendicularly to the optical axis.

4. An imaging optical system according to claim 3 characterised in that at least one of the first and second angle-reducing elements is of a circular cross-section in a plane extending perpendicularly to the optical axis.

5. An imaging optical system according to claim 1 or claim 2 characterised in that the first and second angle-reducing elements are of a rotationally symmetrical cross-section in a plane extending perpendicularly to the optical axis.

6. An imaging optical system according to claim 5 characterised in that the first angle-reducing element has a base surface and the ratio of the diameter of the base surface of the first angle-reducing element to the diameter of the reflecting element is less than 1.

7. An imaging optical system according to claim 6 characterised in that the first angle-reducing element is in the form of any one of a cone and a truncated cone.

8. An imaging optical system according to claim 5 characterised in that the first and second angle-reducing elements are of a circular cross-section in a plane extending perpendicularly to the optical axis.

9. An imaging optical system according to claim 5 characterised in that the first angle-reducing element has a base surface and the ratio of the diameter of the base surface of the first angle-reducing element to the diameter of the reflecting element is between 1/2 and 1/3.

10. An imaging optical system according to claim 9 characterised in that the first angle-reducing element is in the form of any one of a cone and a truncated cone.

11. An imaging optical system according to one of claims 1 and claim 2 characterised in that the second angle-reducing element is formed by a refractive boundary surface of a second transparent body so that angle reduction is effected by refraction of the light beam when the light beam passes into the second transparent body.

12. An imaging optical system according to claim 11 characterised in that the refractive boundary surface includes with the optical axis an angle of between 60° and 120°.

13. An imaging optical system according to claim 11 characterised in that the transparent cylinder is of a height of between 10 mm and 100 mm.

14. An imaging optical system according to claim 11 characterised in that the first angle-reducing element is of a height of between 5 mm and 35 mm.

15. An imaging optical system according to claim 11 characterised in that the refractive boundary surface includes with the optical axis an angle of between 80° and 100°.

16. An imaging optical system according to claim 11 characterised in that the refractive boundary surface includes with the optical axis an angle of between 85° and 95°.

17. An imaging optical system according to claim 11 characterised in that the refractive boundary surface includes with the optical axis an angle of about 90°.

18. An imaging optical system according to claim 11 characterised in that the transparent cylinder is of a height between 20 mm and 90 mm.

19. An imaging optical system according to claim 11 characterised in that the transparent cylinder is of a height between 30 mm and 80 mm.

20. An imaging optical system according to claim 11 characterised in that the transparent cylinder is of a height of 45 mm.

21. An imaging optical system according to claim 11 characterised in that the first angle-reducing element is of a height between 10 mm and 30 mm.

22. An imaging optical system according to claim 11 characterised in that the first angle-reducing element is of a height between 15 mm and 25 mm.

23. An imaging optical system according to claim 11 characterised in that the first angle-reducing element is of a height of 20 mm.

24. An imaging optical system according to one of claims 1 and claim 2 characterised in that the second angle-reducing element is formed by a refractive boundary surface of the transparent cylinder so that angle reduction is effected by refraction of the light beam when the light beam passes into the transparent cylinder.

25. An imaging optical system according to one of claims 1 and 2 characterised in that the first angle-reducing element is formed by a refractive boundary surface of a second transparent body so that angle reduction is effected by refraction of the light beam when the light beam issues from the second transparent body.

26. An imaging optical system according to one of claims 1 and 2 characterised in that the first angle-reducing element is formed by a refractive boundary surface of the transparent cylinder so that angle reduction is effected by refraction of the light beam when the light beam issues from the transparent cylinder.

27. An imaging optical system according to claim 2 characterised in that the ratio of the diameter of the object to be measured relative to the diameter of the reflecting element is less than 1.

28. A peripheral surface sensor for detecting the peripherally extending lateral surfaces of an object comprising an image sensor, and an imaging optical system according to one of claims 1 and 2.

29. A peripheral surface sensor according to claim 28 further comprising a light barrier arrangement which detects the object under the imaging optical system.

30. A peripheral surface sensor according to claim 28 further comprising a lighting means.

31. A peripheral surface sensor according to claim 28 characterised in that the image sensor is a camera that can be operated with a short exposure time.

32. A peripheral surface sensor according to claim 28 characterised in that the image sensor is a camera.

33. A peripheral surface sensor according to claim 28 further comprising an annular lighting means.

34. A peripheral surface sensor according to claim 28 further comprising a lighting means which is provided to produce light flashes.

35. An imaging optical system according to claim 2 characterised in that the reflection surface of the reflecting element is of a circular cross-section in a plane extending perpendicularly to the optical axis.

36. An imaging optical system according to claim 2 characterised in that the ratio of the diameter of the object to be measured relative to the diameter of the reflecting element is between 1/5 and 1/2.

37. An imaging optical system according to claim 2 characterised in that the ratio of the diameter of the object to be measured relative to the diameter of the reflecting element is 1/3.

38. An image optical system according to claim 1 characterised in that reflection occurs on the basis of total reflection of the light beam at the boundary surface.

39. An imaging optical system according to claim 1, characterised in that the boundary surface of the transparent cylinder is mirrored.

40. An imaging optical system according to claim 1 characterised in that the transparent cylinder comprises glass.

41. An imaging optical system according to claim 1 characterised in that the transparent cylinder comprises a transparent plastic material.

42. An imaging optical system according to claim 1 characterised in that the first angle-reducing element comprises metal and the surface of the first angle reducing element is polished.

43. An imaging optical system according to claim 1, characterised in that the surface of the first angle-reducing element is mirrored and the first angle-reducing element comprises at least one material, wherein the material is glass or plastic.

44. An imaging optical system according to claim 1, characterised in that the first angle-reducing element is in the form of a truncated cone, wherein the truncated cone has a continuous central bore extending therethrough.

45. An imaging optical system according to claim 44 characterised in that the transparent cylinder has a second central bore which is arranged concentrically with respect to the central bore of the first angle-reducing element.

46. An imaging optical system according to claim 1 characterised in that the transparent cylinder comprises one of TPX and PE.

47. An imaging optical system according to claim 1 characterised in that the first angle-reducing element comprises aluminium.

48. An imaging optical system according to claim 1 characterised in that the first angle-reducing element comprises metal and its reflecting surfaces are polished.

49. An imaging optical system according to claim 1 characterised in that the first angle-reducing element is the peripheral surface of a truncated cone.

* * * * *

UNITED STATES PATENT AND TRADEMARK OFFICE
CERTIFICATE OF CORRECTION

| | | |
|---|---|---|
| PATENT NO. | : 7,522,277 B2 | Page 1 of 1 |
| APPLICATION NO. | : 10/548922 | |
| DATED | : April 21, 2009 | |
| INVENTOR(S) | : Lehn et al. | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 323 days Delete the phrase "by 323 days" and insert -- by 409 days --

Signed and Sealed this

Twenty-third Day of March, 2010

David J. Kappos
*Director of the United States Patent and Trademark Office*